United States Patent [19]

Garner et al.

[11] 4,102,893
[45] Jul. 25, 1978

[54] PROCESS FOR THE MANUFACTURE OF COLOR FORMERS OF INDOLES AND ANHYDRIDES OF AROMATIC OR HETEROAROMATIC, VICINAL DICARBOXYLIC ACIDS, NEW COLOR FORMERS OF THESE CLASSES OF SUBSTANCE AND THEIR USE

[75] Inventors: Robert Garner, Ramsbottom Bury, England; Max Dunnenberger, Frenkendorf, Switzerland

[73] Assignee: Ciba-Geigy AG, Basel, Switzerland

[21] Appl. No.: 748,012

[22] Filed: Dec. 6, 1976

Related U.S. Application Data

[63] Continuation of Ser. No. 558,598, Mar. 14, 1975, abandoned, which is a continuation of Ser. No. 306,670, Nov. 15, 1972, abandoned.

[30] Foreign Application Priority Data

Nov. 26, 1971 [CH] Switzerland ............. 17239/71
Oct. 12, 1972 [CH] Switzerland ............. 14961/72

[51] Int. Cl.$^2$ ............................................ C07D 209/20
[52] U.S. Cl. .......................... 260/326.14 R; 106/14.5; 106/21
[58] Field of Search ............ 260/326.14 R, 326.13 HD

[56] References Cited

U.S. PATENT DOCUMENTS 3,540,913 11/1970 Lin ..................... 260/326.14 R X
3,736,337 5/1973 Farber ................. 260/326.14 R X
3,931,228 1/1976 Borror ................. 260/326.14 R

FOREIGN PATENT DOCUMENTS 2,257,711 11/1972 Fed. Rep. of Germany ... 260/326.14 R Primary Examiner—Ethel G. Love
Attorney, Agent, or Firm—Edward McC. Roberts; Michael W. Glynn; Prabodh I. Almaula

[57] ABSTRACT

A process for the manufacture of color formers comprising reaction of 2 moles of an indole in the presence of a condensation agent with about 1 mole of an anhydride of the formula

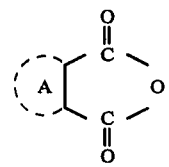

wherein A is the residue of a benzene or naphthalene or of a heterocyclic ring, the new color formers obtained by reacting 2 moles of an indole with a halogen- or nitro-substituted phthalic anhydride, or the anhydride of a vicinal naphthalene pyridine or quinoline dicarboxylic acid, the new 3,3-bis-(indol-3-yl)-phthalides substituted at the nitrogen atom with aralkyl or alkyl with 6 to 18 carbon atoms or alkenyl radicals with 3 to 18 carbon atoms or substituted alkyl or alkylene groups with 1 to 18 and 3 to 18 carbon atoms respectively and pressure sensitive recording paper containing at least one of the new color formers.

8 Claims, No Drawings

PROCESS FOR THE MANUFACTURE OF COLOR FORMERS OF INDOLES AND ANHYDRIDES OF AROMATIC OR HETEROAROMATIC, VICINAL DICARBOXYLIC ACIDS, NEW COLOR FORMERS OF THESE CLASSES OF SUBSTANCE AND THEIR USE

This is a continuation of application Ser. No. 588,598, filed on Mar. 14, 1975, now abandoned, which in turn was a continuation of application Ser. No. 306,670 filed Nov. 15, 1972 (now abandoned).

The present invention relates to a new process for the manufacture of compounds of the formula

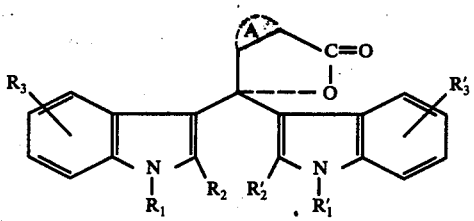

wherein the ring A represents a radical of the benzene or naphthalene series or a heterocyclic radical, in particular a pyridine or quinoline radical, $R_2$ and $R_2'$ each represents hydrogen, low molecular alkyl radicals or aryl radicals, preferably radicals of the benzene series, $R_3$ and $R_3'$ each represents hydrogen, low molecular alkyl or alkoxy groups and $R_1$ and $R_1'$ each represents hydrogen or preferably aralkyl or optionally substituted alkyl or alkenyl radicals with 1 to 18 and 3 to 18 carbon atoms respectively, and to new compounds of this class of substance and their use.

According to Swiss Patent No. 484,251, compounds of this kind may be manufactured in a two-step process. In the first step of this process, 1 mole of an indole was reacted with 1 mole of phthalic anhydride in the presence of a Friedel-Craft catalyst, such as $AlCl_3$, in a solvent, e.g. benzene. The resulting intermediate product was isolated, purified by recrystallisation or chromatographic methods, and then reacted with a further mole of indole in the presence of a condensation agent, e.g. acetic anhydride.

An appreciably simpler process has now been discovered compared with this method of manufacture. The distinguishing feature of this process is that the isolation and purification are omitted. Moreover, the solvent and Friedel-Craft catalyst are no longer required. The two-step synthesis can therefore be replaced by a simple single-step process in which 2 moles of an indole are reacted with approximately 1 mole, preferably 1 to 1.2 moles, of an anhydride of an aromatic or heteroaromatic, vicinal dicarboxylic acid, e.g. of a phthalic anhydride, in the presence of a condensation agent, preferably acetic anhydride.

A series of new compounds which are suitable for use as colour formers have been manufactured by this process. These compounds contain novel anhydride components which are derived from substituted phthalic anhydrides or from heterocyclic anhydrides. A further group of new compounds also comprises those which carry at the indole nitrogen an alkyl group with at least 6 carbon atoms, a benzyl, alkenyl or a substituted alkyl group, e.g. a chloroalkyl, hydroxyalkyl, cyanoalkyl, carbalkoxyalkyl, alkoxyalkyl or carboxyalkyl group.

The invention therefore has for its object a process for the manufacture of compounds of the formula (1), wherein 2 moles of an indole are reacted with about 1 mole, preferably 1 to 1.2 moles, of an anhydride of the formula

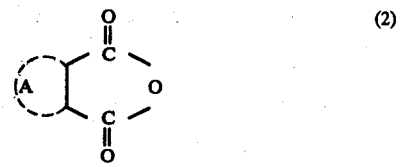

in the presence of an condensation agent.

The ring A in the anhydride component is preferably a benzene ring which is optionally substituted with halogen or nitro, a naphthalene, pyridine or quinoline ring. Particularly preferred on account of their easy accessibility are phthalic anhydride and the halogenated phthalic anhydrides, in particular tetrachlorophthalic anhydride.

The invention also provides new colour formers of the formula

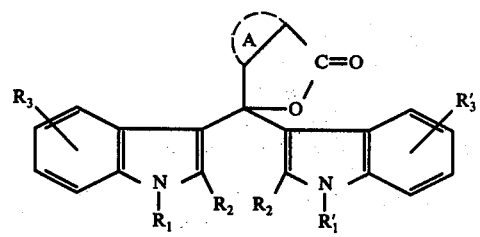

wherein the ring A represents a substituted benzene ring, a naphthalene ring or a heterocyclic ring, $R_2$ and $R_2'$ each represents hydrogen, low molecular alkyl radicals or aryl radicals, preferably radicals of the benzene series, $R_3$ and $R_3'$ each represents hydrogen, low molecular alkyl or alkoxy groups and $R_1$ and $R_1'$ each represents hydrogen or aralkyl or optionally substituted alkyl radicals with 1 to 18 carbon atoms or alkenyl radicals with 3 to 18 carbon atoms, and also in particular the new 3,3-bis-(indol-3-yl)phthalides of the formula

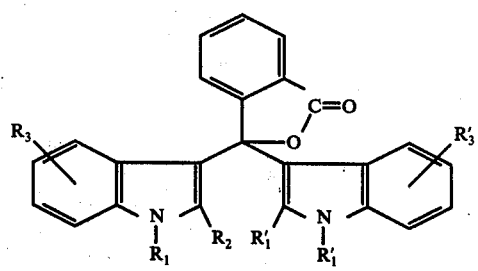

wherein $R_2$ and $R_2'$ each represents hydrogen, low molecular alkyl radicals or aryl radicals, preferably radicals of the benzene series, $R_3$ and $R_3'$ each represents low molecular alkyl or alkoxy groups and $R_1$ and $R_1'$ each represents aralykl or alkyl with 6 to 18 carbon atoms or alkenyl radicals with 3 to 18 carbon atoms or substituted alkyl or alkenyl groups with 1 to 18 and 3 to 18 carbon atoms respectively.

Possible anhydride components in the case of the new compounds corresponding to the formula (1) are phthalic anhydrides which are substituted with nitro or halogen, in particular chlorine, naphthalene-1,2- or 2,3- dicarboxylic anhydrides, and the anhydrides of vicinal pyridine or quinoline-dicarboxylic acids.

As substituents in the 1-position of the indoles prime mention may be made of alkyl, alkenyl and aralkyl, especially benzyl, radicals. The alkyl and alkenyl radicals may contain up to 18 carbon atoms and are optionally substituted, e.g. with chlorine, cyano, hydroxyl, carboxyl, low molecular ester or alkoxy groups. Further substituents of the indoles are preferably in the 2- or 5-position. Those in the 2-position are chiefly low molecular alkyl and aryl radicals, and those in the 5-position are low molecular alkyl or alkoxy radicals. By aryl radicals are meant in particular radicals of the benzene series, such as tolyl, phenyl, chlorophenyl or methoxyphenyl.

As examples of substituted phthalic anhydrides there may be cited:
mononitrophthalic anhydride
3-chloro-, 4-chloro-, 3,4-dichloro-, 3,5-dichloro-, 3,6-dichloro-, 4,5-dichloro-, trichloro-, tetrachloro-, 3-bromo-, 4-bromo-, tribromo, tetrabromophthalic anhydride, tri- and tetrafluorophthalic anhydride.

As examples of suitable indole components there may be cited:
1-allyl-2-methyl-indole,
1-ethyl-2-methyl-indole,
1-ethyl-2-aethyl-indole,
1-ethyl-2-methyl-5-methoxy-indole,
1-propyl-2-methyl-5-ethoxy-indole,
1-butyl-2-methyl-indole,
1-($\beta$-cyanoethyl)-2-methyl-indole,
1-($\beta$-chloroethyl)-2-methyl-indole,
1-($\beta$-carboxyethyl)-2-methyl-indole,
1-($\beta$-hydroxypropyl)-2-methyl-indole,
1-($\beta$-hydroxybutyl)-2-methyl-indole,
1-pentyl-2-methyl-indole,
1-hexyl-2-methyl-indole,
1-benzyl-2-methyl-indole,
1-heptyl-2-methyl-indole,
1-octyl-2-methyl-indole,
1-nonyl-2-methyl-indole,
1-decyl-2-methyl-indole,
1-dodecyl-2-methyl-indole,
1-stearyl-2-methyl-indole,
1-(2'-carboethoxy)-ethyl-2-methyl-indole,
1-(2'-carbopropoxy)-ethyl-2-methyl-indole.

The colour formers are manufactured according to the invention at temperatures between 20° C and the reflux temperature of the reaction mixture. About 1 mole, preferably 1.0 to 1.1 moles, of the anhydride of the formula (2) can be heated with 2 moles of a substituted indole to such a degree that the indole does just not yet boil, preferably to 80° C to 120° C. In this reaction phase the anhydride reacts firstly with one mole of indole. Then a condensation agent, preferably acetic anhydride, is added to the reaction mixture. In this second phase of the reaction, the process is carried out at between 20° and the reflux temperature.

However, it is also possible to carry out the reaction in such a way that the acetic anhydride is added to the mixture of indole and aromatic or heteroaromatic anhydride from the start. In this variant the reaction temperatures are also between 20° C and the reflux temperature. This mode of operation is particularly useful if tetrahalophthalic anhydrides are used.

Upon completion of the reaction, water and then aqueous alkali solutions are added to the resulting cooled mixture. The resulting crude product is isolated by filtration.

The products obtained according to the invention are suitable for use as colour formers, e.g. in pressure sensitive recording materials. Of particular value are the new products which are substituted at the anhydride component, especially the halogenated 3,3-bis(indolyl)-phthalides, because their absoption is displaced in the direction of longer wave-lengths in comparison with the non-substituted products. The new compounds add to the range of available hues.

Also of especial interest are those colour formers according to the invention whose radicals $R_1$ and $R_1'$ contain at least 6 carbon atoms.

The surprising discovery has been made that for the purpose pursued, i.e., the use of the products as colour formers in pressure sensitive recording material, those 3,3-bis-(indolyl)-phthalides are particularly suitable which carry substituents with 6 to 18 carbon atoms at the nitrogen atoms of the indole ring, since they possess favourable solubility properties. In the manufacture of pressure-sensitive recording material, a concentrated solution of the colour former is sealed in microcapsules and these are used as an aqueous suspension for coating the recording material. Common solvents for the manufacture of microcapsules are, for example, hydrated or chlorinated di- or terphenyls. The above cited new 3,3-bis(indolyl)-phthalides are more readily soluble in such solvents than the compounds cited in Swiss Patent No. 484,251. In this group too there is preferably used one of the cited substituted phthalic anhydrides or phthalic anhydride itself.

It is an additional advantage of the new colour formers according to the invention that the coloured designs obtained therewith are suitable for all conventional copying processes.

The pressure-sensitive copying or recording material obtained with the colour formers according to the invention also constitutes an object of the invention. Such copying or reording material consists of at least two sheets and contains at least one of the new colour formers dissolved in an organic solvent and in the form of microcapsules which can be destroyed by pressure, as well as a solid acting as an electron acceptor which is able to convert the dye forming compound into a coloured substance. In general, such recording material consists of a sheet which is coated with the microcapsulated dye and a sheet which is coated with the electron acceptor; these sheets lie with the coated sides on top of each other. By means of pressure, e.g. the pressure of a pencil point, the capsules burst and the colour formers flows on the sheet coated with the electron acceptor, so that a coloured image forms.

As electron acceptor there are preferably used Lewis acids, e.g. alumina, such as attapulgite or phenolic resin preparations.

It is possible to use the colour formers by themselves or in admixture with other already known products, such as crystal violet lactone. They are suitable for the most varied types of pressure-sensitive recording material, e.g. for "chemical transfer", "chemical self-contained" and "monoform" papers. The various systems differ principally in the arrangement of the capsules, the carrier material, and the reagent used for the dye formation. For example, the microcapsules containing the colour formers and the electron acceptor used as reagent can be applied to two different sheets or to the same sheet as coatings. However, they can also be contained in the paper pulp. Such pressure-sensitive papers are described, for example in U.S. Pat. Nos. 3,516,846, 2,730,457, 2,932,582, 3,427,180, 3,418,250 and 3,418,656, and in British Patent Nos. 1,042,597, 1,042,598, 1,042,596, 1,042,599, 1,053,935 and 1,517,650.

The art of microencapsulating has long been known and is described, for example, in the following U.S. Pat. Nos. 2,180,050, 2,800,457, 2,800,458, 3,265,630, 2,964,331, 3,418,656, 3,418,250, 3,016,308, 3,424,827, 3,427,250, 3,405,071, 3,171,878 and 2,797,201. Further methods which are also suitable for the dye forming compounds according to the invention are to be found in British Patent Nos. 989,264 and, above all, 1,156,725.

For the manufacture of the solutions of the colour formers suitable for the encapsulation there are used preferably non-volatile organic solvents, such as polyhalogenated diphenyls, e.g. trichlorodiphenyl and mixtures thereof with liquid paraffin, di-n-butylphthalate, dioctylphthalate, trichlorobenzene, nitrobenzene, petroleum ether, trichloroethylphosphate etc.

Gelatin is frequently used as encapsulating material, as is described for example in U.S. Pat. No. 2,800,457. The formation of the capsule walls about the solution of the colour formers, which is in the form of fine droplets, is accomplished by means of a coacervation process. But it is also possible to manufacture the capsules by a polycondensation of an aminoplast or a modified aminoplast, as is described in British Patent No. 989,264 or 1,156,725.

The capsules are preferably fixed on the carriers material with the aid of a suitable adhesive. Suitable for the purpose are chiefly the conventional coating agents used for paper, e.g. gum arabic, polyvinyl alcohol, hydroxyethyl cellulose, casein, methyl cellulose or dextrin.

The carrier material consists principally of paper, in which connection is meant not only paper of cellulose fibres, but also paper in which the cellulose fibres are replaced wholly or partially by synthetic fibres.

The following Examples illustrate the invention, the parts and percentages being by weight unless otherwise stated and the relationship of parts by weight to parts by volume being the same as that of the gram to the cubic centimeter.

EXAMPLE 1

63.7 g of 1-ethyl-2-methylindole and 32.6 parts of phthalic anhydride are stirred together for 2 hours at 100° C. The mixture is allowed to cool to 50° C, then at this temperature 94 parts by value of acetic anhydride are added thereto and the whole mixture is stirred for 6 hours. Subsequently 300 parts of water are added and the mixture is stirred once more for at least 1 hour. The suspension is neutralised with ammonia and the product is filtered off. The resulting 3,3-bis(1-ethyl-2'-methylindol-3'-yl)-phthalide is washed with water and dried, to give 87 parts of the cited compound (m.p. 231°–232° C) corresponding to 97% of theory. In 95% acetic acid the compound has an absorption maximum at 531 nm.

The compounds listed in the following Table and which correspond to the formula

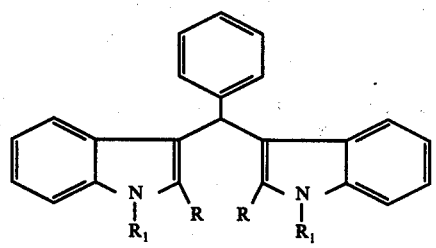

are manufactured in analogous manner:

Table 1

| R | $R_1$ | $R'_1$ | m.p. | λ max. in 95% acetic acid in nm |
|---|---|---|---|---|
| —CH₃ | H | H | 170° | 517 |
| " | —C₄H₉ | —C₄H₉ | 168.5–69.5° | 536 |
| " | —C₅H₁₁ | —C₅H₁₁ | 135–136° | 535 |
| " | —C₆H₁₃ | —C₆H₁₃ | 149–150° | 533 |
| " | —C₇H₁₅ | —C₇H₁₅ | 129–131° | 535 |
| " | —C₈H₁₇ | —C₈H₁₇ | 89–90° | 535 |
| " | —C₉H₁₉ | —C₉H₁₉ | viscous substance | 536 |
| " | —C₁₀H₁₂ | —C₁₀H₁₂ | " | 534 |
| " | —C₁₂H₂₅ | —C₁₂H₂₅ | " | 537 |
| " | —C₁₈H₃₇ | —C₁₈H₃₇ | " | 533 |
| " | —CH₂—CH₂=CH₂ | —CH₂—CH₂=CH₂ | 144–145° | 534 |
| " | —CH₂—CH—CH₃ \| OH | —CH₂—CH—CH₃ \| OH | 138–139° | 527 |
| " | —CH₂—CH—C₂H₅ \| OH | —CH₂CH—C₂H₅ \| OH | 203–204° | 527 |
| " | —C₂H₅ | —C₁₂H₂₅ | viscous substance | 535 |
| H | —C₂H₅ | —C₂H₅ | 258–259° | 517 |
| H | —C₄H₉ | —C₄H₉ | 156–157° | 519 |
| H | —C₆H₁₃ | —C₆H₁₃ | 110–111° | 518 |
| H | —C₈H₁₇ | —C₈H₁₇ | viscous substance | 518 |
| Phenyl | —C₂H₅ | —C₂H₅ | 217–218° | 549 |
| " | —C₄H₉ | —C₄H₉ | 188–189° | 549 |
| " | —C₆H₁₃ | —C₆H₁₃ | 156–157° | 550 |
| " | —C₇H₁₅ | —C₇H₁₅ | 145–146° | 550 |
| " | —C₈H₁₇ | —C₈H₁₇ | 140–141° | 551 |
| " | —C₉H₁₉ | —C₉H₁₉ | 108–109° | 549 |
| " | —C₁₂H₂₅ | —C₁₂H₂₅ | 89–90° | 551 |

EXAMPLE 2 a) 15.9 parts of 1-ethyl-2-methylindole, 15.7 parts of tetrachlorophthalic anhydride and 30 parts by volume of acetic anhydride are stirred together for 6 hours at 100° C. The reaction mixture is worked up as described in Example 1 and the product is additionally washed with methanol before being dried. The yield is 26.7 parts of 3,3-bis-(1'-ethyl-2'-methylindol-3'-yl)-4,5,6,7-tetrachlorophthalide (m.p. 216°-217° C). This corresponds to a yield of 91% of theory.

b) By substituting a corresponding amount of 1-decyl-2-methylindole for 1-ethyl-2-methylindole, there is obtained in the same way 3,3-bis-(1'-decyl-2'-methylindole-3'-yl)-4,5,6,7-tetrachlorophthalide (m.p. 153°-154° C).

The indolyltetrachlorophthalides of the formula

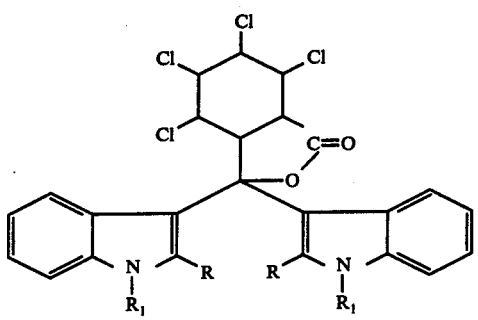

wherein $R_1$ and R have the meanings given in the following Table, are obtained in analogous manner:

Table 2

| R | $R_1$ | m.p. | λ max in 95% acetic acid in nm |
|---|---|---|---|
| H | —$C_4H_9$ | 209–210° | 524 |
| H | —$C_6H_{13}$ | 148–149° | 520 |
| —$CH_3$ | —$C_2H_5$ | 231–232° | 554 |
| —$CH_3$ | —$C_3H_7$ | 196–197° | 559 |
| " | —$C_4H_9$ | 236–237° | 560 |
| " | —$C_5H_{11}$ | 183–184° | 560 |
| " | —$C_6H_{13}$ | 183–184° | 560 |
| " | —$C_7H_{15}$ | 185–186° | 559 |
| " | —$C_8H_{17}$ | 193–194° | 560 |
| " | —$C_9H_{19}$ | 172–173° | 551 |
| " | —$C_{10}H_{21}$ | 138–140° | 563 |
| " | —$C_{12}H_{25}$ | 152–153° | 558 |
| " | —$C_{18}H_{37}$ | viscous substance | 558 |
| " | —$CH_2$—CH=$CH_2$ | 225–226° | 560 |
| " | —$CH_2$—$CH_2$—CN | 196–197° | 559 |
| " | H | 292–293° | 538 |

Table 2-continued

| R | $R_1$ | m.p. | λ max in 95% acetic acid in nm |
|---|---|---|---|
| " | —$C_2H_4$—$COOC_2H_5$ | 118–119° | 560 |
| | H | 309–310° decomposition | 570 |
| —$CH_3$ | —$C_2H_5$ | 277–278° " | 563 |
| " | —$C_3H_7$ | 250° decomposition | 565 |
| " | —$C_4H_9$ | 230–231° decomposition | 566 |
| " | —$C_5H_{11}$ | 206–207° decomposition | 563 |
| " | —$C_6H_{13}$ | 208–209° decomposition | 565 |
| " | —$C_7H_{15}$ | 199–200° decomposition | 565 |
| " | —$C_8H_{17}$ | 170–171° decomposition | 565 |
| " | —$C_9H_{19}$ | 141–142° decomposition | 565 |
| " | —$C_{12}H_{25}$ | 98–99° decomposition | 566 | by using a mononitrophthalic anhydride instead of tetrachlorophthalic anhydride, the following dyestuffs of the formula

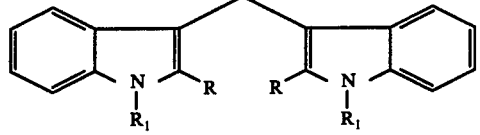

are obtained by the process described in Example 2.

| R | $R_1$ | m.p. | λ max in 95% acetic acid in nm |
|---|---|---|---|
| —$Ch_3$ | —$C_2H_5$ | 238–239° | 546 |
| —$CH_3$ | —$C_8H_{17}$ | 118–119° | 544 |
| —$CH_3$ | —$C_{12}H_{25}$ | 107–108° | 545 |
| -phenyl | —$C_2H_5$ | 260–261° | 550 |
| -phenyl | —$C_8H_{17}$ | 181–182° | 555 |
| -phenyl | —$C_8H_{17}$ | 247–248° | 554 |

If in Example 2 an equivalent amount of the anhydride cited in column I of the following Table is substituted for tetrachlorophthalic anhydride, the compounds listed in column II are obtained.

Table 4

| I | II | m.p. | λmax in 95 % acetic acid in nm |
|---|---|---|---|
| naphthalene-3,4-anhydride | 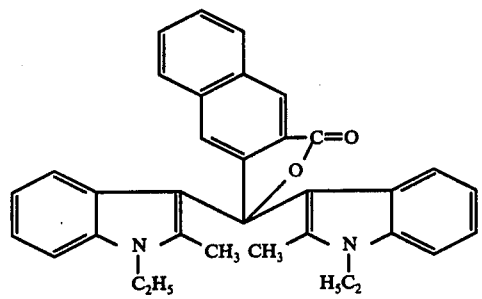 | 146 – 147° | 533 |

Table 4-continued

| I | II | m.p. | λmax in 95% acetic acid in nm |
|---|---|---|---|
| tetrabromophthalic anhydride | (structure with tetrabromo phthalide bis-indole, N-C₂H₅ groups, CH₃ CH₃) | 234 – 235° | 562 |
| 1,4-dichoro-phthalic anhydride | (structure with 1,4-dichloro phthalide bis-indole, N-C₂H₅ groups, CH₃ CH₃) | 270 – 272° | 557 |
| pyridine-2,3-dicarboxylic anhydride | (structure with pyridine-fused phthalide bis-indole, N-C₂H₅ groups, CH₃ CH₃) | 204 – 205° | 552 |

EXAMPLE 3

12 parts of gelatin are dissolved in 88 parts of water and a solution of 3 parts of the colour former described in Example 2 a) in 100 parts of trichlorophenyl is added at 50° C and the mixture is emulsified. While stirring, a solution of 12 parts of gum arabic in 88 parts of water is added. The emulsion is diluted with 200 parts of water at 50° C and then, while stirring, poured at the same temperature into 700 parts of water. The coacervation is brought to completion by cooling the mixture to 10° C and stirring it at this temperature for 3 hours. The resulting aqueous suspension of microcapsules, which contain the solution of the colour former, is used for coating a sheet of paper. A second sheet is coated with attapulgite or a phenolic resin preparation.

When the two sheets with the coated sides are laid against each other and the uncoated side of the sheet that carries the dye forming compound is written upon with pressure, the microcapsules burst and the solution of the colour former passes on to the second sheet, on which a reddish violet, clear and sharp copy of the writing appears.

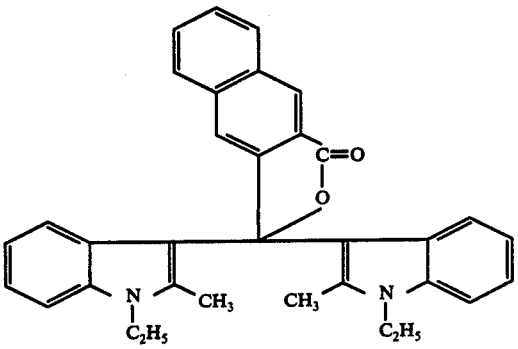

We claim:
1. A compound of the formula

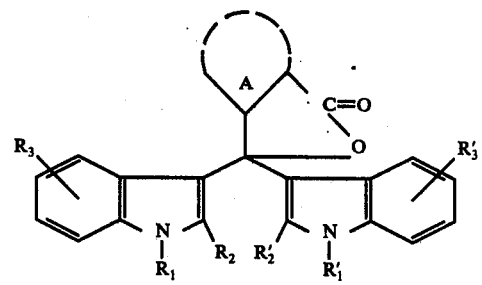

wherein the ring A is benzene or benzene substituted with halogen or nitro,
$R_2$ and $R_2'$ each independently represent hydrogen, lower alkyl, or phenyl,
$R_3$ and $R_3'$ each independently represent hydrogen, lower alkyl or lower alkoxy, and
$R_1$ and $R_1'$ each independently represent alkyl of 6 to 18 carbon atoms.

2. 3,3-bis-(indol-3-yl)-phthalides of the formula

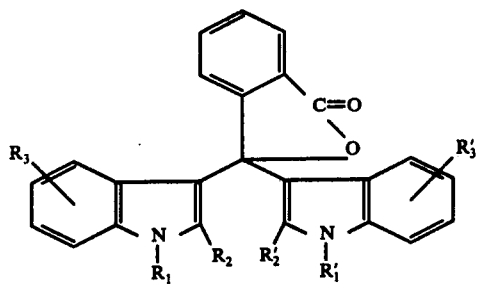

wherein
R_2 and R_2' each independently represent hydrogen, lower alkyl, or phenyl,
R_3 and R_3' each independently represent hydrogen, lower alkyl or lower alkoxy, and R_1 and R_1' each independently represent alkyl of 6 to 16 carbon atoms.

3. A compound according to claim 2, wherein R_2 and R_2' represent lower alkyl, and R_3 and R_3' represent hydrogen or lower alkoxy.

4. A compound according to claim 1 wherein the ring A is tetrachlorophenyl and R_2 and R_2' are hydrogen or methyl.

5. A compound according to claim 2, wherein R_2 and R_2' each are methyl, R_3 and R_3' each are hydrogen and R_1 and R_1' each are n-octyl.

6. A compound according to claim 2, wherein R_2 and R_2' each are methyl, R_3 and R_3' each are hydrogen and R_1 and R_1' each are n-hexyl.

7. A compound according to claim 1, wherein ring A is tetrachlorophenyl, R_2 and R_2' each are methyl, R_3 and R_3' each are hydrogen and R_1 and R_1' each are n-octyl.

8. A compound of the formula: